(12) United States Patent
Cormier

(10) Patent No.: US 12,029,618 B2
(45) Date of Patent: Jul. 9, 2024

(54) SURGICAL TOOL HOLDING AND POSITIONING DEVICE

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventor: Philip Cormier, Newburyport, MA (US)

(73) Assignees: Smith & Nephew, Inc, Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 357 days.

(21) Appl. No.: 17/402,193

(22) Filed: Aug. 13, 2021

(65) Prior Publication Data

US 2022/0047351 A1     Feb. 17, 2022

Related U.S. Application Data

(60) Provisional application No. 63/066,630, filed on Aug. 17, 2020.

(51) Int. Cl.
*A61B 90/50* (2016.01)
*A61B 17/00* (2006.01)

(52) U.S. Cl.
CPC ........ *A61B 90/50* (2016.02); *A61B 17/00234* (2013.01)

(58) Field of Classification Search
CPC .... A61B 17/00234; A61B 2017/00212; A61B 2017/00398; A61B 90/361; A61B 90/50
See application file for complete search history.

(56) References Cited

U.S. PATENT DOCUMENTS

| | | | |
|---|---|---|---|
| 2002/0083603 A1* | 7/2002 | Jang | G01C 15/002 33/286 |
| 2007/0229655 A1 | 10/2007 | Ellison et al. | |
| 2015/0133958 A1 | 5/2015 | Singh et al. | |
| 2015/0257629 A1 | 9/2015 | Shahinian | |
| 2016/0290387 A1 | 10/2016 | Richman | |

* cited by examiner

*Primary Examiner* — Mohamed G Gabr
(74) *Attorney, Agent, or Firm* — Norman F. Hainer, Jr.; Kate Ryland Tetzlaff

(57) ABSTRACT

A surgical tool positioning device for positioning and holding a surgical tool is disclosed. The device includes an adjustable-friction ball and socket joint configured to provide three degrees of rotational freedom. A variable holding force may be applied to the ball via a locking member to selectively lock and unlock the adjustable-friction ball and socket joint. The socket includes a friction-inducing member housed therein and in contact with the ball. When the ball and socket joint is unlocked, this friction-inducing member provides sufficient frictional force to hold a position of the surgical tool. However, this frictional force may be overcome with intentional external forces such as during repositioning of the surgical tool.

19 Claims, 6 Drawing Sheets

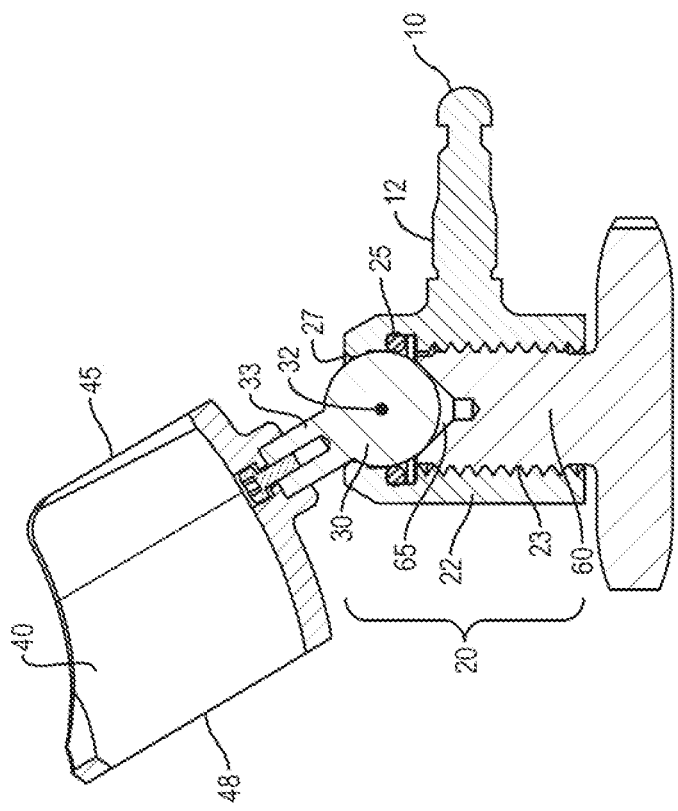

SURGICAL TOOL HOLDING AND POSITIONING DEVICE

CROSS-REFERENCE TO RELATED APPLICATIONS

This application claims benefit to and incorporates by reference in its entirety, US Provisional Patent No. 63/066,630, filed Aug. 17, 2020 and titled "SURGICAL DEVICE HOLDING AND POSITIONING DEVICE".

FIELD OF THE INVENTION

The present invention relates generally to the field of medical instrument supports, and more specifically to a repositionable medical tool positioning device.

BACKGROUND

During surgery, such as orthopedic arthroscopic surgery, multiple tools such as a light source, arthroscope, and surgical tools may all be used simultaneously. This can present a challenge to the surgeon. Surgeons require a third hand to hold and/or manipulate at least one of the tools, or separate means of holding and, in some cases, repositioning at least one of the tools. The physician's assistant (PA) may perform this task, limiting them from doing anything else at this time. Therefore, there is a need for a system that holds, repositions, and maintains that position, without the need for an assistant.

BRIEF DESCRIPTION OF THE DRAWINGS

For a detailed description of example embodiments, reference will now be made to the accompanying drawings in which:

FIG. 1E schematically shows a cross section view of the positioning device illustrated in FIG. 1A, in a locked and angled configuration, in accordance with this disclosure;

SUMMARY

Figure 1B:
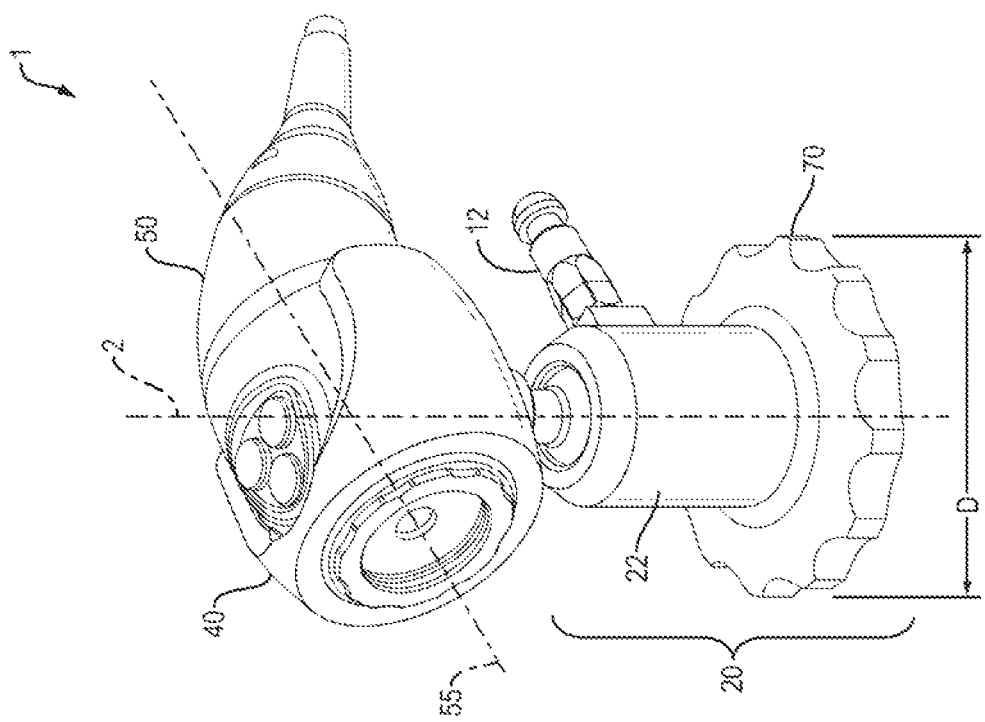
FIG. 1B schematically shows an assembled view of the positioning device illustrated in FIG. 1A, and assembled with an example surgical tool (camera) in accordance with this disclosure.

Various terms are used to refer to particular system components. Different companies may refer to a component by different names—this document does not intend to distinguish between components that differ in name but not function. In the following discussion and in the claims, the terms "including" and "comprising" are used in open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Generally this system is a positioning device that rigidly holds a surgical tool such as a camera head. The camera head may have an arthroscope mounted thereto. Other tools may include a retractor or light source for example. The positioning device allows three degrees of rotational freedom so that the surgical tool may be moved to a desired orientation and then held or locked in that orientation. The positioning device includes a means of adjusting the frictional hold on the positioning device, and a means of maintaining a lower threshold level of friction, different from the means of adjusting. The lower threshold frictional hold is preferably sufficient to require an external force beyond the weight of the surgical tool on the positioning device. Stated in another way, when the surgeon releases hold of the surgical tool and positioning device in any orientation, the surgical tool is prevented from slipping or flopping out of the target position by the means maintaining the lower threshold friction. The positioning device may be coupled to a positioning arm (not shown) that may be rigidly attached to a surgical table rail or to a separate positioning arm, independent of the surgical table.

The specification now turns to an example device. Various embodiments are directed to a device for positioning and holding a surgical tool during arthroscopic surgery. The device includes a docking station for receiving and holding a surgical tool. An adjustable-friction ball and socket joint is coupled to the docking station moveable to provide three degrees of rotational freedom while orienting the docking station and surgical tool. The adjustable-friction ball and socket joint includes a ball member that may include an outer convex surface along two primary axes. Outer convex surface may include a spherical portion. The socket nests the ball member and may be disposed at a first end of a housing of the device. A friction-inducing member is disposed within the housing and in contact with the ball member. This friction-inducing member applies a first friction force on the ball outer surface, that may be overcome when an external positioning force is applied to the surgical tool or docking station. The surgeon may grab the surgical tool or docking station to move its position to a target orientation by overcoming this first frictional force. This first frictional force is provided by the friction-inducing member in contact with the ball member and is sufficient to keep the docking station and surgical tool stationary upon release of the external positioning force. The weight for example will not drag the surgical tool orientation away from the target orientation. The device also includes a locking member configured to move relative to the ball member and apply a variable friction force on the ball member. This locking member applies a supplemental friction force to the first friction force to lock the surgical tool in position. When locked, the external position force is significantly greater to change the orientation of the surgical tool.

In some example devices, the docking station may directly couple to the ball member. A stem portion of the ball member may couple directly to the docking station. The housing may include a tubular portion, the socket defining a first end of the tubular portion and a second opposing end of the tubular portion configured to operatively couple to the locking member. The locking member may include a concave shaped end for receiving a portion of the ball member therein. The friction-inducing member may include at least one selected from the group consisting of an O-ring, an X-ring, a U-ring, a C-ring, an E-ring, a gasket, a ball seal, a sleeve and a diaphragm. The frictional-inducing member may extend circumferentially around an inner surface of the socket. The locking member is moveable between an unlocked configuration and a locked configuration. In the unlocked configuration, no or minimal load is applied by the locking member on the ball member. In the unlocked configuration, the docking station and surgical tool may be moved and oriented to the target location and held in place by the first frictional force. The entire locking member may be spaced away from the ball member in the unlocked configuration. The friction-inducing member contacts the ball member at a location below a center of the ball member. The locking member may threadingly engage a threaded bore of the housing, the bore coaxial with a center of the ball member. The locking member may include a concave cavity sized to circumferentially contact the ball member and forming a void between the ball member disposed within the concave cavity, and a bottom surface of the concave cavity.

Another example medical instrument support device for positioning and holding a surgical tool during arthroscopic surgery is disclosed herein. This device includes a docking station for receiving a surgical tool therein. It also includes an adjustable-friction ball and socket joint coupled to the docking station and configured to provide three degrees of rotational freedom during positioning of the surgical tool. The adjustable-friction ball and socket joint includes a ball member having a convex outer surface along two primary axes. The adjustable-friction ball and socket joint also includes a tube having a first end defining a socket for receiving the ball member therein. The tube second opposing end includes a threaded locking member moveable along the tube. An end of the locking member is moveable to selectively engage an outer surface of the ball member, and lock the ball and socket joint in place. The tube first end also includes a friction-inducing member, nested within a recess within the tube. The friction-inducing member engages the ball member with a first frictional force. The locking member includes an actuator that rotates the locking component and applies an adjustable frictional force on the ball member to selectively increase friction on the ball member greater than the first frictional force.

In some example devices the friction-inducing member is configured to frictionally engage an outer portion of the ball member and limit unintended rotation about three degrees of movement of the ball member. The ball member defines a center point and the friction-inducing member may be disposed around the outer surface of the ball member and axially spaced from or offset from the center point. The locking component includes a concave cavity sized to apply an axial load around an outer circumferential surface of the ball member and apply a minimal load to the ball member that is disposed within the concave cavity. The docking station extends from the ball member and comprises a flexible portion configured to flex and allow the surgical tool to be inserted into and couple to the docking station.

An example method of positioning and holding a surgical tool during arthroscopic surgery is disclosed. The method includes operatively coupling a surgical tool to a docking station of a positioning system. With a locking member of the positioning device in an unlocked configuration, an external force is applied on at least one of the surgical tool and docking station to rotate a ball member within a socket of the positioning device and thereby rotate the surgical tool and docking station around at least one of three degrees of freedom to a target orientation. The external force is sufficient to overcome a first frictional force between the ball member and a friction-inducing member circumferentially disposed and in contact with the ball member. The first frictional force is sufficient to maintain the surgical tool in the target orientation upon release of the external force. The locking member is adjusted to a locking hold configuration to lock the surgical tool and docking station in the target location.

In some example methods, adjusting the locking member includes axially moving a concave surface of the locking member to engage an outer circumferential surface of the ball member. In some example methods, the locking member is spaced away from the ball member in the unlocked configuration. In some example methods, adjusting the locking member includes rotating the locking member to move the locking member along a tubular portion of the positioning device. The example method may further comprising changing the orientation of the surgical tool to a second, different orientation by adjusting the locking component back to the unlocked configuration; and then applying an external force on at least one of the surgical tool and docking station to rotate the ball member within the socket portion of the positioning device and thereby rotate the surgical tool and docking station around at least one of three degrees of freedom to the second target orientation. The external force is sufficient to overcome the frictional force between the ball member and the friction-inducing member. This frictional force is sufficient to maintain the docking station and surgical tool in the second orientation upon release of the external reorienting force. The locking member is adjusted back to a locking hold configuration to lock the surgical tool and docking station in the second target orientation. While the ball rotates within the socket, the friction-inducing member may remain stationary.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Generally, this disclosure describes a positioning device that allows the surgeon to connect a surgical tool, such as a camera head, to a surgical positioning arm (not shown). The surgical positioning arm may include a rail attached to or integral with a surgical table, or may be a separate positioning arm, independent of the surgical table. The surgical positioning arm and positioning device may be either manually controlled or at least partially controlled by a robotic device, remotely controlled by the surgeon. For example, the surgeon could, via remote software, control the positioning device's orientation in space. The surgeon could also roughly manually position the device and then perform fine adjustments via remote software. As a further example, the positioning device's orientation could also manipulated by electric motors that are controlled by the surgeon via remote software. In addition to controlling device orientation (roll, pitch, yaw), electric motors could also be used to perform fine adjustments (x, y, z motions) to position via remote software.

The surgeon may adjust the orientation of the surgical tool, around at least three axes, relative to the surgical positioning arm via the positioning device and rigidly hold the surgical tool relative to the surgical positioning arm thereby creating a hands-free scenario. Generally, this positioning device includes a connecting means to the surgical positioning arm, a cradle or docking station to hold a surgical tool such as a camera head, and an adjustable and lockable means of moving and holding an orientation of the surgical tool.

Figure 1A:
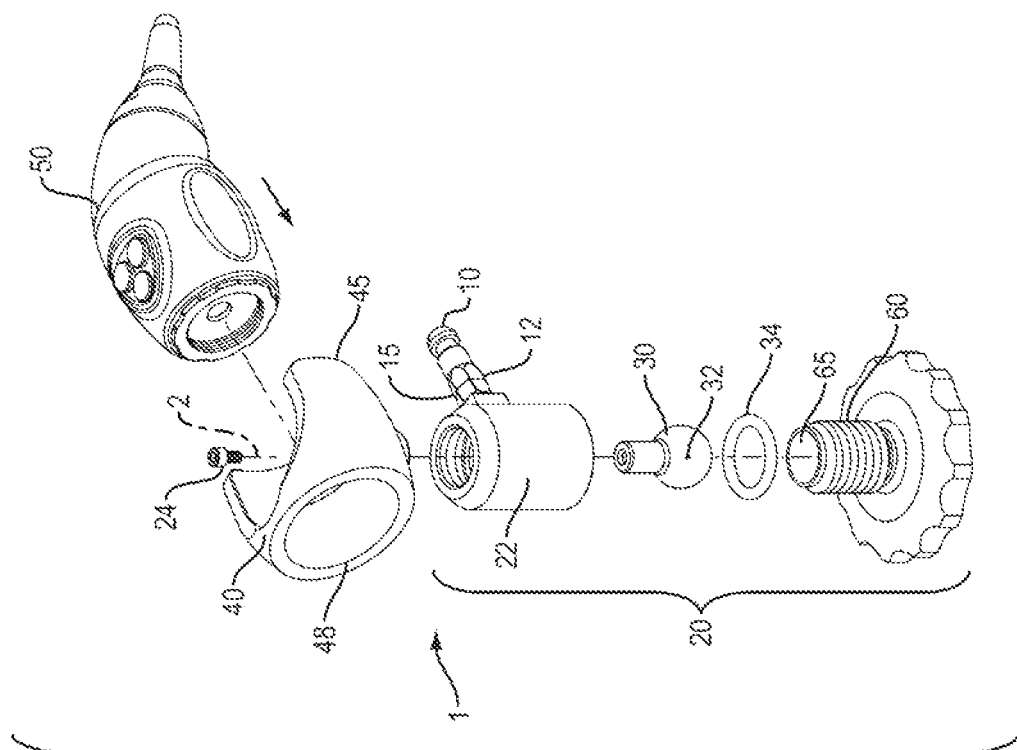
FIG. 1A schematically shows an exploded view of a positioning device including an example surgical tool (camera) in accordance with this disclosure.
Figure 1D:
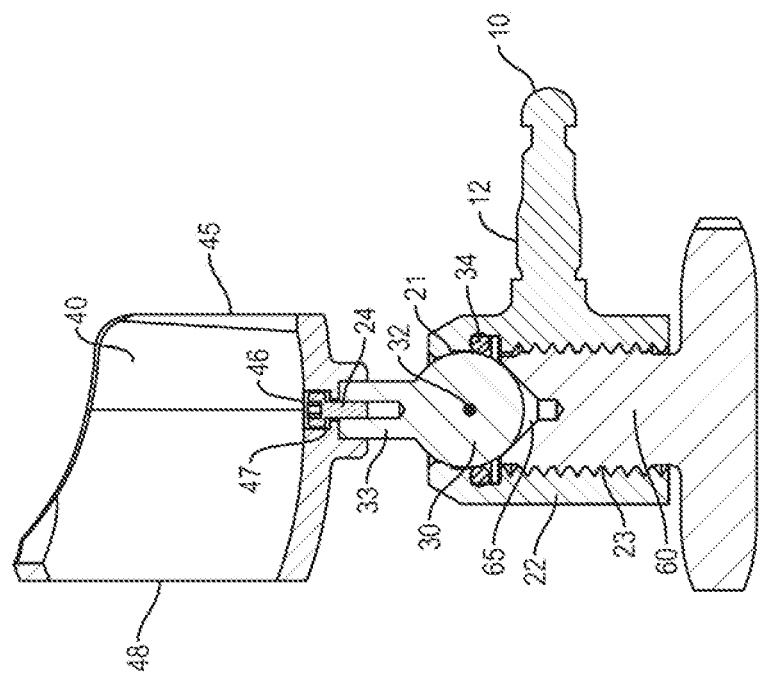
FIG. 1D schematically shows a cross section view of the positioning device illustrated in FIG. 1A, and in a locked configuration, in accordance with this disclosure.

Turning to a more specific embodiment, FIG. 1A illustrates an exploded view of a positioning device 1 for positioning and holding a surgical tool such as a camera head 50. Device 1 may include a connection means 10 configured to rigidly connect the device 1 to a surgical positioning arm (surgical arm not shown). Device 1 may also include an adjustable and lockable ball and socket joint construct 20 that may allow the surgical tool to be rotated about up to three axes (3 degrees of rotational freedom) relative to the surgical positioning arm. The device 1 also includes a docking station 40 configured to assemble a surgical tool such as a camera head 50 with the positioning device 1. This docking station 40 may be specific to a particular surgical tool shape or camera head. The surgical positioning arm (not shown) may be similar to the Spider 2 Arm offered by Smith and Nephew Inc.

Shown in FIGS. 1A-1E, connection means 10 may be a post 12 that may be selectively inserted into a mating feature on a surgical positioning arm (not shown). Post 12 may be integral with the joint construct 20, and more specifically may be integral or directly coupled to an outer cylindrical housing 22 of construct 20. Post 12 may extend substantially perpendicular relative to a longitudinal axis 2 of cylindrical housing 22 and may include a series of notches or keys 14, 16, that aid in coupling the post 12 to a mating portion of the surgical positioning arm. Post 12 may include a hexagonal portion 15 to limit rotation of post 12 within corresponding mating feature of arm. Post 12 may define a longitudinal axis that extends laterally from the cylindrical housing 22. The post longitudinal axis may intersect the longitudinal axis 2 of the cylindrical housing 22 at a location spaced along the cylindrical housing longitudinal axis 2 that is axially spaced away from the ball 30 (best seen in FIGS. 1C and 1D). Stated otherwise, the ball joint 30 defines a center 32 disposed within the cylindrical housing 22 at a location spaced along the cylindrical housing 22 longitudinal axis 2 at a location axially spaced from a longitudinal axis of the post 12. The longitudinal axis of the post 12 intersects the longitudinal axis 2 at a location on an opposite side of the ball 30 to the docking station 40.

Docking station 40 may be a snap fit with zero toggle to facilitate a rigid hold of the camera head 50. Camera head 50 may dock with docking station 40 through a rear opening that may define an opening size slightly smaller in width or diameter than the anticipated surgical tool (50) to be inserted therein; and thereby by a zero toggle fit. Rear opening 45 may extend around or wrap around and above the centerline 55 of the anticipated tool 50 thereby wedging the tool 50 into the front opening 48. The force created by this interference is sufficient to hold the tool (camera) steady when the surgeon locks the ball and socket joint construct 20 and releases hold of the tool (camera). Docking station 40 may be formed of a polymer material, configured to minimally flex and permit docking of the camera head 50, but sufficiently rigid to hold the camera head 50 with zero toggle. Materials including but not limited to ABS, Polycarbonate, PC-ABS, Macrolon, PTFE, PEEK or PEI.

The front opening 48 may be a completely continuous 360 degree bounded hole, preventing the front portion 48 from splaying open while maintaining a thin wall thickness. The docking station 40 shown best in FIGS. 1A-1B may have a contoured inner surface, configured to conform to the outer surface contours of the intended tool such as camera head 50.

Docking station 40 may be rigidly coupled to adjustable ball and socket joint construct 20 using mechanical means such as a screw 24. Docking station 40 may be rigidly coupled to a stem 33 of ball 30 using mechanical means such as a screw 24. Screw 24 may extend through a bore 46 in the lower portion of the docking station 40 and into a threaded cavity of a stem 33 extending from ball 30. Bottom surface of docking station 40 may include a countersink 47 to receive a cylindrical stem 33 therein. Stem 33 may include a threaded lumen to threadingly couple to screw 24. Seen best in FIG. 1A, the ball 30 may be passed up through the cylindrical housing 22 before it is connected to the docking station 40. The external shape of stem 33 could also be hexagonal, square, D-shape, etc. so as to prevent unintentional rotation between it and docking station 40. Alternative mechanical means to screw 24 may include a press fit, bolts or permanent attachment means such as a weld.

Figure 1C:
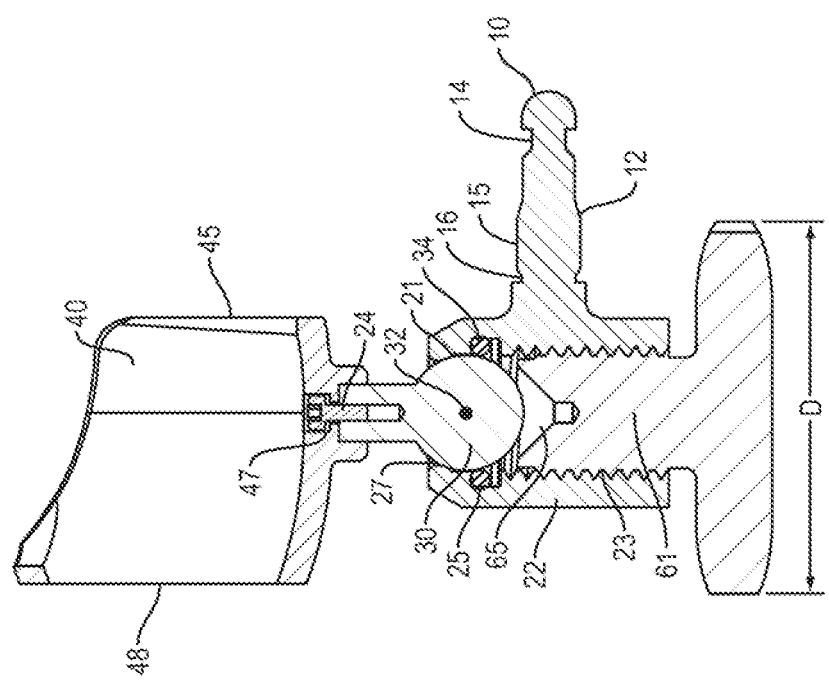
FIG. 1C schematically shows a cross section view of the positioning device illustrated in FIG. 1A, and in a loose hold configuration, in accordance with this disclosure.
Figure 2B:
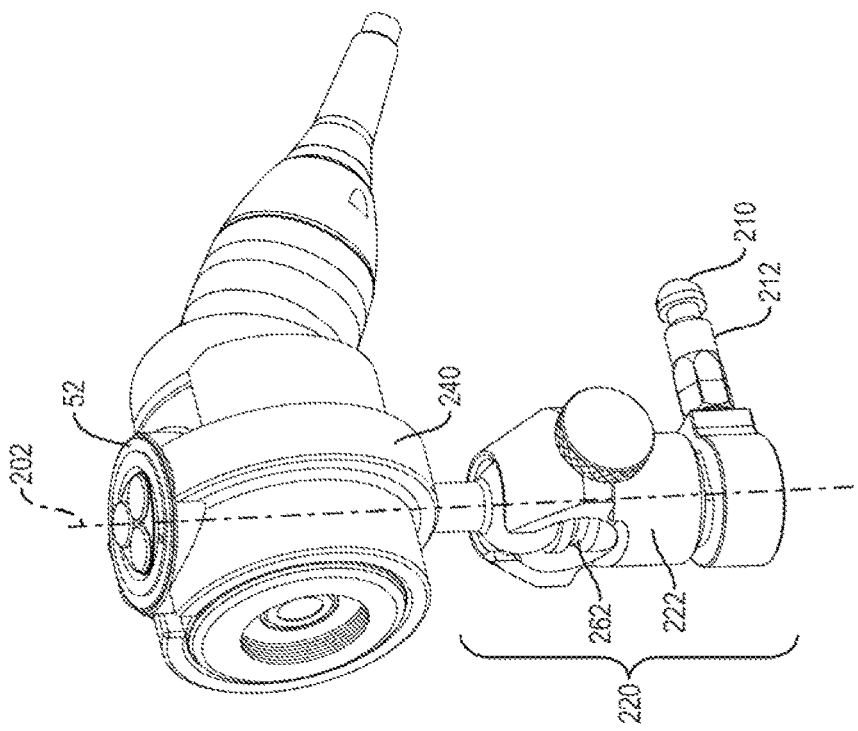
FIG. 2B schematically shows an assembled view of the embodiment illustrated in FIG. 2A, in accordance with this disclosure.
Figure 2A:
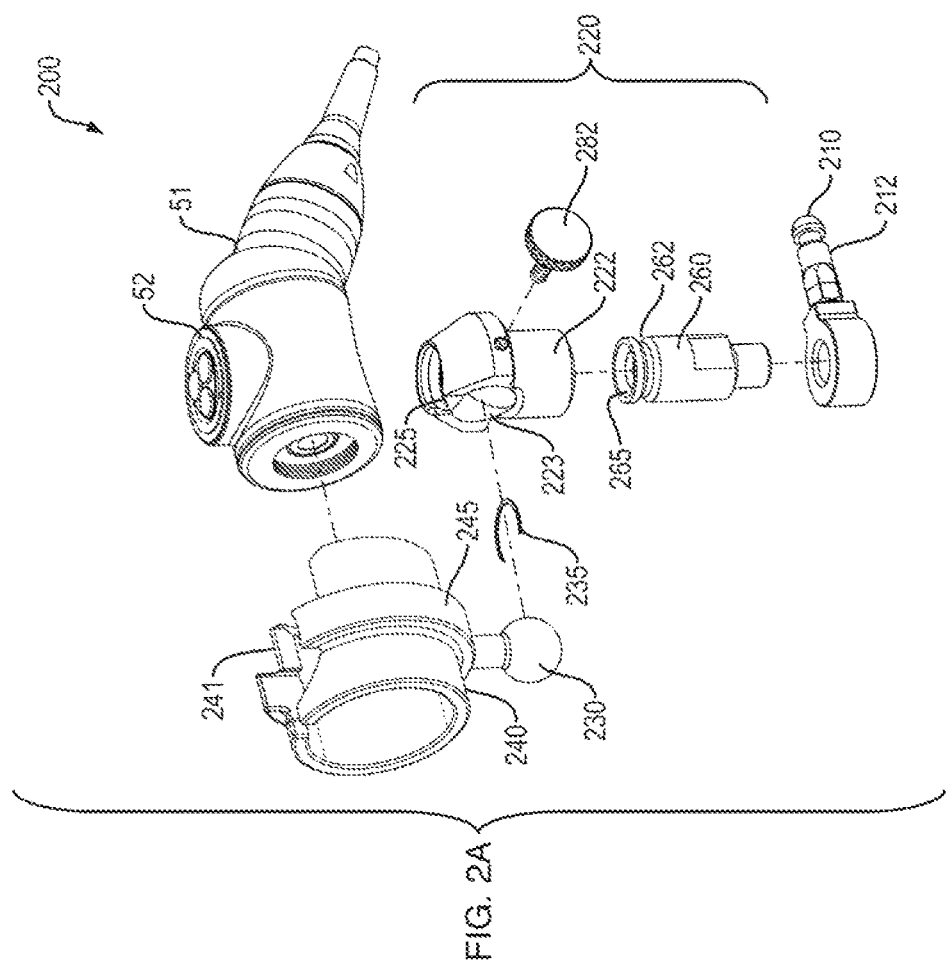
FIG. 2A schematically shows an exploded view of a second embodiment of a positioning device including an example surgical tool (camera) in accordance with this disclosure.
Figure 2D:
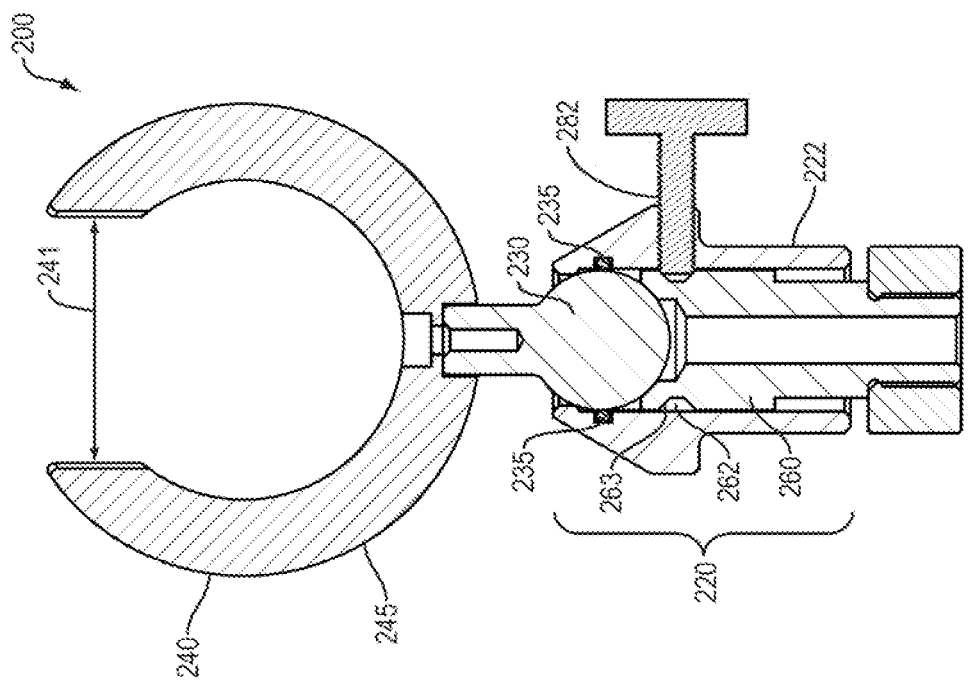
FIG. 2D schematically shows another cross section view of the second embodiment, in accordance with this disclosure.
Figure 2C:
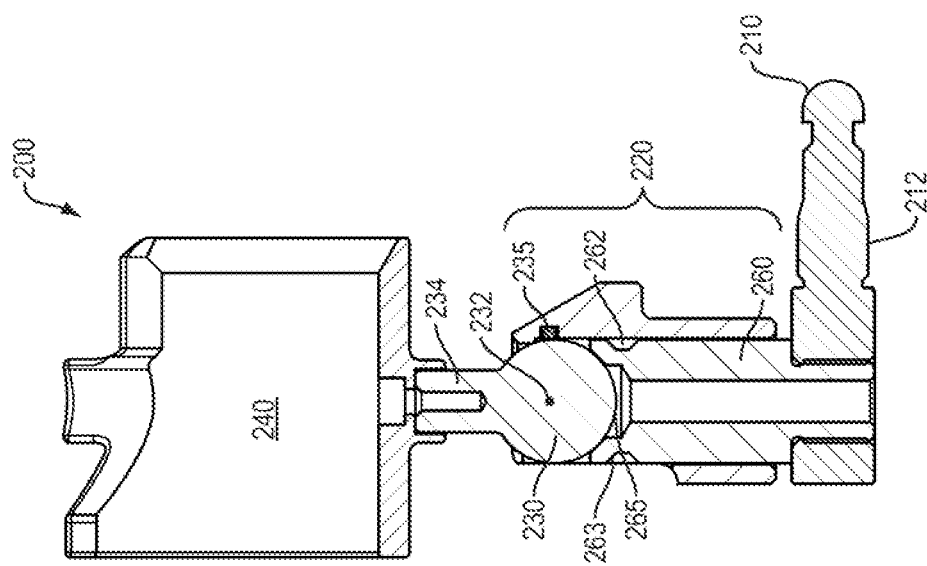
FIG. 2C schematically shows a cross section view of the second embodiment, in accordance with this disclosure.

Adjustable ball and socket joint construct 20 is configured to provide up to three degrees of rotational freedom while positioning and orienting the surgical tool. Ball 30 may be spherical or egg shaped, and defines a symmetrical body with outer convex surface along at least a portion of the ball 30. Ball 30 is configured to rotate within a socket at least partially around three axes. Socket may be defined by a portion of a bore 23 through the cylindrical housing 22. Bore 23 may also include a friction-inducing means such as an O-ring 34 concentrically disposed around the longitudinal axis 2 of the cylindrical housing 22. O-ring 34 is in direct contact around an outer surface of ball 30 to apply a frictional force to the ball 30 thereby creating a drag force when the joint construct 20 is in a loose or relatively unlocked configuration (described below). The O-ring 34 may be at least partially recessed within an annular cavity 25 within the bore 23, the annular cavity 25 having a larger maximum diameter than the local bore diameter, such that O-ring 34 is partially recessed relative to the bore 23. O-ring 34 encircles and engages the spherical portion of ball 30 at a location offset from and below the ball center 32 thereby creating a compressive force on the ball 30. This O-ring 34 is configured such that when the ball and socket joint is loose, as shown in FIG. 1C and the docking station is moved to a first orientation such as the orientation shown in FIG. 1E, the docking station with or without a surgical tool assembled therein, remains in this first orientation due to frictional engagement between the O-ring and ball outer surface. The load of the docking station and any tool 50 docked therein preferably does not overcome the frictional drag between the O-ring 34 and ball outer surface. Stated otherwise, if the user releases hold of the positioning device while the joint construct 30 is in the loose configuration at any orientation (FIG. 1C/1E), the friction inducing member 34 resists unintended motion and thereby the orientation is maintained. However, the frictional force is not so great that positioning or orienting the docking station 40 and thereby any tool assembled therein requires excessive force by the user.

O-ring 34 may have a variety of cross sections, such as a circular, oval, "X" or "U" cross section. Alternative frictional inducing members may include gaskets, diaphragms (flat or rolling), Bal Seals, Bal Springs, or discs. These members may be disposed within the bore 23 and partially wrapped around the outer surface of the ball 30 to provide resistance to unintentional motion. Diaphragms or discs may be elastomeric or a flexible metal/plastic with a higher frictional surface attribute, to alter the frictional characteristics within the joint and reduce the joint's likelihood of sagging. As a further alternative, an elastomeric sleeve may be disposed along a length of the bore 23 and between the ball 30 and inner surface of bore 23, again with surface attributes to alter the frictional characteristics within the joint 20 and reduce the joint's likelihood of sagging.

In some example embodiments, the ball and socket joint construct 20 may include a friction-inducing means such as surface treatments such as a friction inducing texture. This texture may be on a portion of the outer surface of the ball 30, and/or the bore 23 and/or a portion of locking component 60. For example, a high friction surface texture or treatment may be added to an inner surface of bore 23 that engages the outer surface of ball 30. A high friction surface may include a bead blast or aluminum oxide blast surface. As a further example or additionally, a high friction surface treatment may be added to a distal end of locking component 60 such as a portion of concave cavity 65 that selectively engages the ball 30. Alternatively, high friction coatings may be added to a portion of at least one of an inside surface of bore 23 that engages the ball 30, the locking component distal end, or outer surface of spherical structure of ball joint 30. Coatings or surface texture treatments may be in the form of a continuous surface area around a substantial portion of the ball 30, bore 23 or locking component 60, or may be formed in rings or a plurality of discrete portions around at least one the surfaces. Surface treatments or coatings may eliminate the need to add extra steps or cavities within the bore 23 to house an extra component such as an O-ring. Surface treatments or coatings may be in addition to the friction inducing member 34.

To lock the adjustable joint construct 20, the locking member 60 is translated axially along the longitudinal axis 2. The locking member 60 may be spaced away from the ball or lightly engage the ball 30 when the device is in a loose or unlocked configuration, as shown in FIG. 1C. It is in this unlocked configuration, that the docking station 40 and surgical tool may be positioned in a target orientation and then maintain this target orientation while still in the unlocked configuration via the frictional forces provided by the friction inducing member 34, members and/or friction inducing means. Moving the locking member 60 to engage the ball 30 may tighten the frictional hold on the ball 30 such that repositioning requires a higher external force.

Bore 23 may include internal threads configured to receive and threadingly engage with shaft 61 of a threaded locking member 60. The locking member 60 may include an actuation handle 70 at a first end and a concave cavity 65 at an opposing end. Concave cavity 65 may be cone shaped, stepped, concave or may alternatively be a completely hollow core defining a through-lumen through a portion of the entire locking component 60. Concave cavity 65 may partially nest a portion of the ball 30 therein in the locked configuration, seen best in FIG. 1D. Cavity 65 defines an outer rim that engages the outer surface of the ball 30 and applies a uniform pressure around a surface of the ball 30, compressing ball 30 between the locking member 60 and a step 21 in the cylindrical housing's inner bore 23. Step 21 forms a smaller internal opening size of the bore 23 at a first end, relative to the opening size along a second, opposing end. Step 21 forms a smaller internal opening size of the bore 23 retaining ball 30 within the socket. It is preferable that the axial locking component 60 not engage a lower most portion adjacent and including the lower apex or bottom surface of the ball 30 disposed within the cavity. Therefore the cavity 65 is shaped to limit engagement with the outer surface of the ball 30 and thereby apply an axial locking force around a wider portion of the ball 30 while maintaining a gap and thereby not contacting and engaging the cavity internal surface with the portion of the ball 30 within the cavity 65.

The threaded locking member 60 is preferably axially aligned with the longitudinal axis 2 of housing 22, to apply an axial locking load on the ball and socket joint 20. Actuation handle 70 may be a knob with a diameter greater than threaded shaft 61 to provide a greater mechanical advantage and the potential for a greater locking force on the joint 20. This direct axial loading is preferable as it has a greater mechanical advantage than lateral loading on the ball 30 and therefore creates a more reliable lock. Actuation handle 70 may be a turning control, to rotate the threaded locking member 60 and translate the concave cavity 65 to vary the pressure or frictional force on the ball 30. Actuation control 70 may define a maximum diameter D that is larger than a maximum diameter of the cylindrical housing 22. In addition, unintentionally unlocking or loosening of the frictional hold on the ball 30 is reduced with this locking component due to the frictional resistance of the threaded shaft with the threaded bore 23. Depending on the thread pitch, a greater degree of control of locking load may be provided. For example, a lower thread pitch, or a higher threads per inch (TPI) may allow for a finer degree of loading control. Additionally, a finer thread pitch has a reduced thread helix angle and therefore more efficiently transfers the tightening torque applied by the user on actuation handle 70 into an axial force. Since each rotation of the locking component 60 directly transfers to an axial load onto the ball 30, and is not a component or portion of this load as described in the second embodiment herein, the inventor envisions that this in line/direct axial control is preferable to ensure strong locking loads on the joint construct 20

The cylindrical housing 22 may include a chamfer 27 at the top of the bore 23 adjacent the ball 30 to increase the cone of angulation of the docking station 40 relative to the housing 22. This is illustrated in FIG. 1E where chamfer 27 may abut the stem 33 at a more extreme docking station orientation. Chamfer 27 provides a relief, allowing for larger orientation angles relative to the longitudinal axis 2 during positioning of the docking station and tool assembled therein. Preferably, the components of the device listed above may be reusable and sterilizable by means readily available in a hospital setting, e.g. an autoclave. The device positioner may also be delivered to the operating room as a sterile packaged single use device. Lastly, the components may be available in a combination of single use sterile packaged or reusable and sterilizable.

A method of positioning a surgical tool may therefore include coupling a positioning device 1 to a positioning arm or rail, which may include inserting a lateral post 12 into a mating feature on the positioning arm or rail. This may further include engaging a locking channel 14 with a corresponding component of the positioning arm or rail. A surgical tool may then be coupled to a docking station 40 of the positioning device 1. For example a camera head 50 may be slid into a rear opening 45 of a docking station 40 of the positioning device 1, the camera head 50 slightly larger than the rear opening 45 such that the rear opening flexes to allow entry. The camera head 50 may be inserted into an enclosed circular front opening such that the camera head 50 is encircled by a contoured cradle configured to wrap around and above a centerline of the camera head body and thereby engage the camera head body with a toggle free fit. An axial locking component 60 may be actuated to rotate and translate the locking component along a longitudinal axis 2 of a cylindrical housing of the device 1 towards a ball joint of the device. A concave end 65 of the locking component may is spaced slightly away from or loosely engaged with a ball portion of a ball and socket joint construct 20 of the device 1, defining a loose or unlocked configuration. The docking station 40 and thereby the surgical tool may then be orientated or moved to a target orientation which may include rotating the surgical tool around three degrees of freedom. The surgeon may grip an external surface of docking station 40 to orient the surgical tool to the target orientation. With the device 1 in the loose or unlocked configuration, and the surgical tool in the target orientation, an external grip or hold on the docking station 40 may be released. (The surgeon may release hold of the device). Drag provided by a friction inducing member, such as an O-ring and/or surface treatment disposed within the cylindrical bore and in contact with the ball allows for the docking station and thereby the surgical tool to maintain this target orientation without the surgeon needing to hold the device. The gravitational loads or weight of the docking station and surgical tool combined are insufficient to move the docking station. The axial locking component 60 may then be turned and axially translated, engage the ball 30 and increasing the frictional hold on the ball 30. This may lock the docking station 40 and thereby the surgical tool in the target orientation.

FIGS. 2A-2D schematically show an alternative embodiment of a surgical tool-positioning device 200. Similar to the previous embodiments, positioning device 200 may include three components: a connection means 210 configured to rigidly connect the positioning device 200 to the surgical positioning arm or rail (not shown); an adjustable and lockable ball and socket joint construct 220 that allows the surgical tool such as camera head 51 to be rotated around three axes relative to the surgical positioning arm; and a docking station 240 configured to rigidly connect a camera head 51 to the positioning device 200. In this embodiment the docking station 240 is designed specifically for an alternate camera body 51. The docking station 240 makes use of a boss 52 on the top of the camera head body to facilitate a snap fit that remains toggle free when the surgeon releases their grip on the camera. In this embodiment the docking station 240 is also split defining a gap 241 at the top (best seen in cross section FIG. 2D) allowing the docking station 240 to spread and snap around the boss 52. A rib 245 may be added as a strengthening feature so that the snap fit has sufficient force to hold the tool 51, toggle free. In addition the ball joint 230 may be integral to the docking station 240. Side opening 223 is disposed through the side wall of the cylindrical housing 222 to allow the spherical structure 230 access to the housing bore 223.

Similar to the embodiment shown in FIGS. 1A-1E, connection means 210 may be a post 212 that may be selectively insertable into a mating feature on a surgical positioning arm (not shown). Post 212 may be integral with the adjustable joint 220 and may extend substantially perpendicularly relative to a longitudinal axis 202 of cylindrical housing 222 and may include a series of notches or keys, that aid in coupling the post 212 to a mating portion of the surgical positioning arm. Post 212 may define a longitudinal axis that intersects the adjustable joint 222 at a location spaced away from the ball joint 230. Stated otherwise, the ball joint 230 defines a center 232 and is disposed within the cylindrical housing 222 at a location spaced along the cylindrical housing longitudinal axis at a location axially spaced from the shaft 212. Post 212 may extend laterally and preferably perpendicularly from the longitudinal axis of the stem 234 of ball joint 230, to orient the surgical tool 51 in a preferable location relative to the connecting post 212, thereby placing the surgical tool in a preferable and easier to manipulate position relative to the surgical arm or rail.

Adjustable joint 220 may also include a C-ring 235 concentrically disposed within the cylindrical housing 222 and around a bore 223. C-Ring 235 is similar to other friction inducing members disclosed herein and is configured to apply pressure and a frictional resistance to the ball joint 230 when the joint 220 is in a loose or relatively unlocked configuration. The C-ring 235 may be at least partially recessed within an annular cavity 225 within the cylindrical housing 222 and may be disposed at or below the center 232 of the ball joint 230 thereby creating a small compressive force on the ball joint 230.

Alternatives or additional embodiments may include friction-inducing means such as surface treatments including textures and/or coatings, or discs, diaphragms etc, configured to fit within the bore and increase drag between the ball and socket to resist unintentional sagging or motion of the joint upon release in the loose configuration.

This embodiment also includes a side loading locking mechanism including a nut 282 that extends through a wall of the cylindrical housing 222 to operatively engage with an outer surface of the adjustable mechanism 220 and locking the adjustable mechanism 222 and thereby the camera head 51 is the desired orientation. The cylindrical housing 222 has a bore coaxial with the cylindrical longitudinal axis and configured to receive a locking component 260 therein. The locking component 260 may include a concave cavity 265, similar to concave cavity 65 described in previous embodiment. Component 260 may be integral with connection post 212 or coupled thereto. Component 260 may include a circumferential channel 262 disposed around an outer circumferential surface of the component 260, the channel 262 having a sloped or chamfered top surface 263. Chamfered top surface 263 acts as a camming surface to axial slide component 260 upwards to apply a variable load on the ball 230, and thereby lock the adjustable ball and socket joint construct 220 in the desired orientation.

In some example embodiments not shown, the joint construct may pivot about a cylinder instead of a spherical structure (not shown). If a single cylinder were used then the motion would be about a single axis. The addition of a second or third cylinder perpendicular relative to the first cylinder may allow rotation about a second and third axis respectively. The plurality of cylinders could then be locked either simultaneously or individually in a similar manner as the sphere in the preferred embodiment.

Figure 3B:
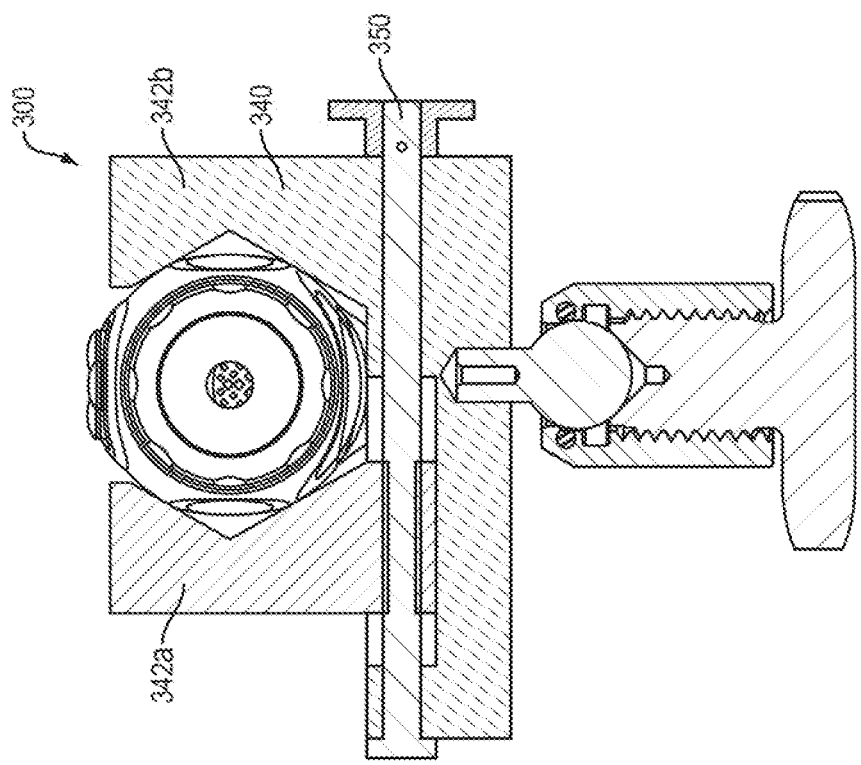
FIG. 3B schematically shows a cross section view of the third embodiment in a locked configuration, in accordance with this disclosure.
Figure 3A:
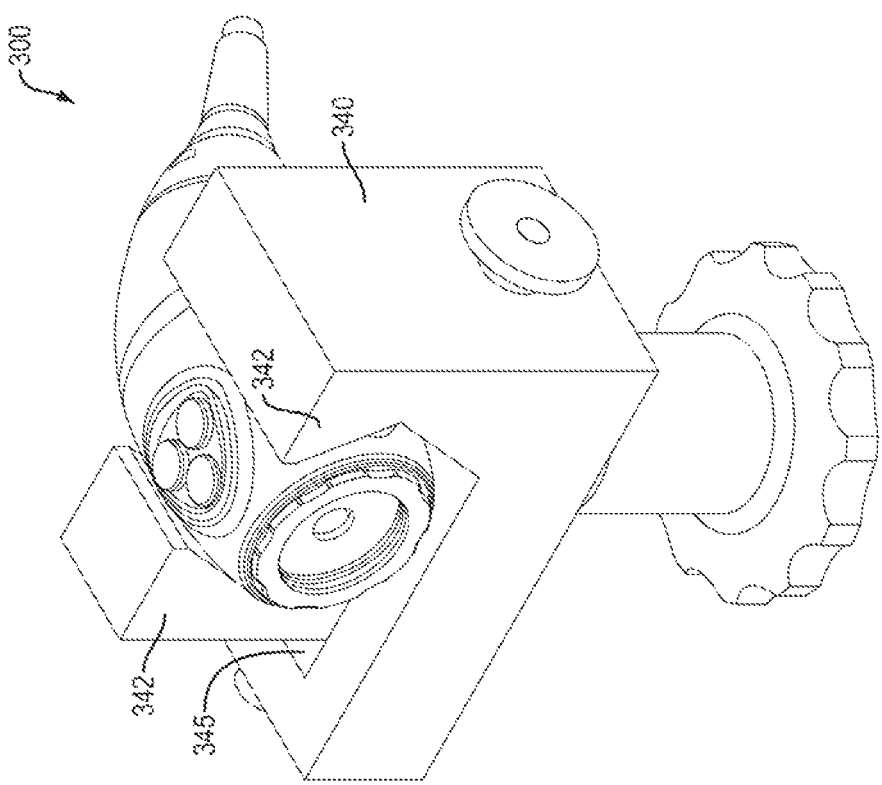
FIG. 3A schematically shows an assembled view of a third embodiment of a positioning device assembled with an example surgical tool (camera), in accordance with this disclosure.

Another example embodiment of a docking station 340 is shown in FIGS. 3A and 3B. The docking station 340 consists of a set of v-grooves 342 offset from each other and with one of the v-grooves set into a slot 345 so that it may slide thereby allowing the mechanism to adapt to a range of tool sizes. A first v-groove 342*a* may be attached to a sliding component 350, to slide and engage a surgical tool and force it to engage with a second v-groove 342*b* opposite the first v-groove 342*a*. In alternative embodiments, the v-groove may be a slot, a flat face, or a segment of a cylinder. In further alternative embodiments, the v-grooves may not be rigidly attached to the slide mechanism; they may also be attached via a cylinder or spherical connection that allows them to pivot thereby better matching the orientation of the camera head. Alternatively, the slide mechanism may be controlled by a threaded shaft that pulls or pushes the slide mechanism attached to one of the v-grooves. Embodiment 300 may include a ball and socket construct similar to construct 20 or 220.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A device for positioning and holding a surgical tool during arthroscopic surgery comprising:
   a docking station configured to operatively couple to the surgical tool; and
   an adjustable-friction ball and socket joint coupled to the docking station and configured to provide three degrees of rotational freedom during positioning of the surgical tool, the adjustable-friction ball and socket joint comprising:
     a ball member having a spherical outer surface;
     a socket configured to nest the ball member, the socket defined in a first end of a housing;
     a friction inducing member disposed within the housing and in contact with the spherical outer surface of the ball member, the friction inducing member configured to apply a first friction force on the spherical outer surface, the first friction force configured to be overcome when an external positioning force is applied to move the surgical tool while assembled to the docking station to a target orientation, while also configured to resist unintended movement when the external positioning force is released; and
     a locking member having a concave shaped end for receive a portion of the ball member therein, the locking member configured to move relative to the ball member and apply a variable friction force on the ball member that is supplemental to the first friction force to selectively lock the surgical tool while assembled to the docking station in position.

2. The device of claim 1 wherein the docking station couples directly to the ball member.

3. The device of claim 1 wherein the housing includes a tubular portion, the socket defining a first end of the tubular portion and a second opposing end of the tubular portion configured to operatively couple to the locking member.

4. The device of claim 1 wherein the friction inducing member comprises at least one selected from the group consisting of an O-ring, an X-ring, a C-ring, an E-ring, a U-ring, a gasket, a ball seal, a sleeve and a diaphragm.

5. The device of claim 1 wherein the friction-inducing member is configured to circumferentially extend around an inner surface of the socket.

6. The device of claim 1 wherein the locking member is moveable between a loose hold configuration and a locking hold configuration, in the loose hold configuration the entire locking member may be spaced away from the ball member.

7. The device of claim 1 wherein the friction-inducing member contacts the ball member at a location below a center of the ball member.

8. The device of claim 1 wherein the locking member threadingly engages a threaded bore of the housing, the threaded bore coaxial with a center of the ball member.

9. The device of claim 1 wherein the locking member concave shaped end circumferentially contacts the ball member, forming a void between the ball member disposed within the concave shaped end, and a bottom surface of the concave shaped end.

10. A device for positioning and holding a surgical tool during arthroscopic surgery comprising:
    a docking station configured to receive a surgical tool therein; and
    an adjustable-friction ball and socket joint coupled to the docking station and configured to provide rotational freedom during positioning of the surgical tool, the adjustable-friction ball and socket joint comprising;
      a ball member having a convex outer surface;
      a tube having a first end defining a socket for receiving the ball member therein and a second opposing end configured to receive a threaded locking member therein, the threaded locking member moveable along the tube and configured to engage an outer circumferential surface of the ball member;
      a friction inducing member nested within the tube and configured to engage the ball member with a first frictional force; and
      an actuator operatively coupled to the locking member to rotate the threaded locking member and apply an adjustable frictional force on the ball member to selectively increase friction on the ball member greater than the first frictional force.

11. The device of claim 10 wherein the friction inducing member is configured to frictionally engage the convex outer surface and limit unintended rotation of the ball member.

12. The device of claim 10 wherein the ball member defines a center point and wherein the friction-inducing member is disposed around the outer surface of the ball member and axially offset from the center point.

13. The device of claim 10 wherein the locking component includes a concave cavity sized to apply an axial load around an outer circumferential surface of the ball member and apply a reduced load to a portion of the ball member disposed within the concave cavity.

14. The device of claim 10 wherein the docking station extends from the ball member and comprises a flexible portion configured to flex and allow the surgical tool to be inserted into and couple to the docking station.

15. A device for positioning and holding a surgical tool during arthroscopic surgery comprising:
    a docking station configured to operatively couple to the surgical tool; and
    an adjustable-friction ball and socket joint coupled to the docking station and configured to provide three degrees of rotational freedom during positioning of the surgical tool, the adjustable-friction ball and socket joint comprising:

a ball member having a spherical outer surface;

a socket configured to nest the ball member, the socket defined in a first end of a housing;

a friction inducing member disposed within the housing and in contact with the spherical outer surface of the ball member, the friction inducing member configured to apply a first friction force on the spherical outer surface, the first friction force configured to be overcome when an external positioning force is applied to move the surgical tool while assembled to the docking station to a target orientation, while also configured to resist unintended movement when the external positioning force is released; and a locking member configured to move relative to the ball member and apply a variable friction force on the ball member that is supplemental to the first friction force to selectively lock the surgical tool while assembled to the docking station in position, and wherein the locking member includes a concave cavity sized to circumferentially contact the ball member, while forming a void between the ball member disposed within the concave cavity and a bottom surface of the concave cavity.

16. The device of claim 15 wherein the docking station couples directly to the ball member.

17. The device of claim 15 wherein the housing includes a tubular portion, the socket defining a first end of the tubular portion and a second opposing end of the tubular portion configured to operatively couple to the locking member.

18. The device of claim 15 wherein the friction-inducing member is configured to circumferentially extend around an inner surface of the socket.

19. The device of claim 15 wherein the locking member threadingly engages a threaded bore of the housing, the threaded bore coaxial with a center of the ball member.

* * * * *